United States Patent [19]

Van Poucke et al.

[11] 4,342,825

[45] Aug. 3, 1982

[54] PHOTOGRAPHIC ELEMENTS CONTAINING CYAN-FORMING COLOR COUPLERS

[75] Inventors: Raphaël K. Van Poucke, Berchem; Marcel J. Monbaliu; Jan J. Vandewalle, both of Mortsel, all of Belgium

[73] Assignee: AGFA-GEVAERT N.V., Mortsel, Belgium

[21] Appl. No.: 247,404

[22] Filed: Mar. 25, 1981

[30] Foreign Application Priority Data

Apr. 9, 1980 [GB] United Kingdom ............... 8011693

[51] Int. Cl.$^3$ .......................... G03C 1/76; G03C 1/40
[52] U.S. Cl. .................................. 430/505; 430/552; 430/553
[58] Field of Search .................... 430/505, 552, 553

[56] References Cited

U.S. PATENT DOCUMENTS

| | | | |
|---|---|---|---|
| 2,895,826 | 7/1959 | Salminen et al. | 430/552 |
| 3,880,661 | 4/1975 | Lau et al. | 430/552 |
| 4,009,035 | 2/1977 | Kojima et al. | 430/552 |
| 4,012,258 | 3/1977 | Kojima et al. | 430/552 |
| 4,124,396 | 11/1978 | Osborn | 430/553 |
| 4,299,914 | 11/1981 | Fujimatsu et al. | 430/553 |

*Primary Examiner*—J. Travis Brown
*Attorney, Agent, or Firm*—A. W. Breiner

[57] ABSTRACT

Cyan-forming phenol type color couplers comprising in the 2-position of the phenol a benzamido group carrying on the benzene nucleus of the benzamido group at least one —Q—Rf group wherein Q is —O—, —S—, or —SO$_2$—, and Rf is a short-chain fluorine-containing group derived from hexafluoropropylene or trifluorochloroethylene.

These cyan-forming color couplers can be incorporated in (a) red-sensitized silver halide emulsion layer(s) of a photographic multilayer color element or in a non-light-sensitive colloid layer in water-permeable relationship with the red-sensitized emulsion layer(s).

5 Claims, No Drawings

PHOTOGRAPHIC ELEMENTS CONTAINING CYAN-FORMING COLOR COUPLERS

The present invention relates to novel cyan-forming colour couplers, to the use thereof in the production of photographic colour images, and to photographic elements containing such couplers.

It is known that for the production of a photographic colour image in a light-sensitive silver halide layer, the exposed silver halide is developed to a silver image by means of an aromatic primary amino compound in the presence of a colour coupler, which reacts with the oxidized developing substance to form a dyestuff at the areas corresponding to the silver image.

In subtractive three-colour photography use is made of a light-sensitive photographic colour element comprising (a) red-sensitized silver halide emulsion layer(s), (a) green-sensitized silver halide emulsion layer(s), and (a) blue-sensitive silver halide emulsion layer(s), wherein upon colour development, by the use of appropriate colour couplers, cyan, magenta, and yellow dyestuff images are formed respectively.

Fundamental difficulties affecting the subtractive three-colour photographic process are concerned primarily with the stability of the dyes, which make up the coloured photographic images, against light, heat, and humidity. Although colour photography has undergone much improvement since the appearance of the use of coupler compounds for the formation of coloured images, higher dye stability is still wanted.

An important factor in the production of colour images is the cost of the light-sensitive element and consequently of its components and in particular of the colour couplers.

Many attempts have been made to provide new colour couplers having improved characteristics. For instance, the U.S. Pat. No. 2,895,826 discloses a class of colour couplers including cyan-forming couplers, which contain a perfluorobutyramido group and, owing to this group, confer to the dyes formed favourable light-absorption characteristics and stability. A serious drawback of these couplers is that in their preparation for the introduction of the perfluorobutyramido group, the very expensive perfluorobutyryl chloride has to be used.

DT-OS 2,515,771 teaches the use of colour couplers comprising a monohydro-polyfluoroalkyl group wherein the hydrogen atom is in the ω-position. The synthesis of such couplers is also very expensive.

It is an object of the present invention to provide novel cyan-forming colour couplers, which have improved properties and at the same time are very interesting from an economical standpoint.

A further object is to provide photographic colour elements containing said novel cyan-forming colour couplers.

Another object of the invention is to produce a photographic colour image by development of a photographic multilayer colour element containing said novel cyan-forming colour couplers.

Other objects of the invention will become apparent from the disclosure hereinafter.

The above objects are accomplished with the aid of novel fluorine-containing cyan-forming colour couplers, which have been prepared from a comparatively inexpensive starting product, have favourable sensitometric results, and have a high coupling activity, the dyes obtained therewith after coupling being very stable to light, heat, and humidity.

According to the present invention there are provided novel phenol-type colour couplers capable of forming a cyan indoaniline dye by reaction with an oxidized aromatic primary amino developing agent and carrying a fluorine containing substituent, wherein said couplers comprise in the 2-position of the phenol a benzamido group carrying on its benzene nucleus at least one —Q—Rf group as fluorine-containing substituent, Q being oxygen, sulphur, or sulphonyl, and Rf representing a short-chain fluorine-containing group derived from hexafluoropropylene or trifluorochloroethylene, such short-chain group corresponding to one of the formulae —$CF_2$—CHFY, —CF=CFY, or —$CF_2$—CF=$CF_2$, Y being chlorine or trifluoromethyl.

More particularly, in accordance with the present invention there are provided novel cyan-forming colour couplers corresponding to the following general formula I:

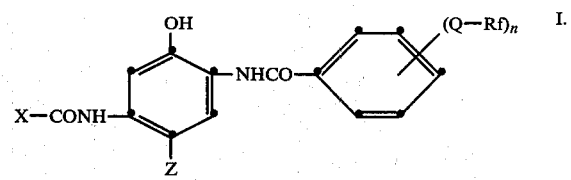

wherein:
Q and Rf have the significances given hereinbefore,
n represents an integer of at least 1, preferably 1, 2, or 3,
Z represents a hydrogen atom in the case of 4-equivalent couplers or a substituent, the so-called coupling off group, that splits off upon colour development, thus conferring to the colour coupler a 2-equivalent character e.g. a halogen atom such as chlorine, an acyloxy group, an alkoxy group, an aryloxy group, a heterocycloxy group, an alkylthio group, an arylthio group e.g. phenylthio and carboxyphenylthio, an alkylsulphonyl group, an arylsulphonyl group, an alkylsulphinyl group, an arylsulphinyl group, an alkyl- or aryl-substituted carbonylmethoxy group, an alkoxy- or aryloxy-substituted carbonylmethoxy group, a heterocyclic thio group, and a phenylazo group, and X is a ballasting group of sufficient size rendering said colour coupler non-diffusing in an alkali-permeable layer of a photographic element; in particular a group corresponding to the general formula II:

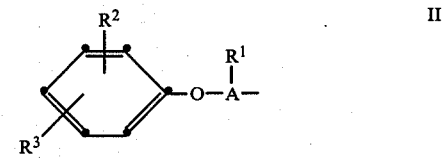

wherein:
A is a $C_1$–$C_5$ alkylene group e.g. methylene or propylene,
$R^1$ is hydrogen or a $C_1$–$C_5$ alkyl group e.g. methyl, ethyl, or butyl,
$R^2$ is a halogen atom e.g. chlorine, an alkyl group e.g. tert-butyl, tert-pentyl, n-dodecyl, n-tetradecyl, or n-pentadecyl, an alkoxy group e.g. n-dodecyloxy, or a cycloaliphatic group e.g. cyclopentyl, $R^3$ is hydrogen or an alkyl group e.g. tert-butyl, tert-pentyl, or n-tetradecyl, or $R^2$ and $R^3$ together represent the atoms needed to complete a fused on cycloaliphatic ring or a fused on cycloaliphatic ring that is substituted by up to 4 alkyl groups e.g. a tetramethylcyclopentane ring.

The present invention also provides a photographic colour element comprising at least three silver halide emulsion layers, which are differently optically sensitized and wherein the novel colour coupler(s) as set forth above is (are) present in the red-sensitized silver halide emulsion layer(s) or in a non-light-sensitive colloid layer in water-permeable relationship therewith.

The novel cyan-forming colour couplers containing a benzamido group that carries on the benzene nucleus of the benzamido group at least one short-chain fluorine-containing group as specified above are prepared from benzoyl chloride starting products, which carry at least one such fluorine-containing group and which are far less expensive than the comparable acid chlorides having a perfluoroalkyl group.

The mono-, di-, or tri-(fluoroalkyl-oxy)-substituted benzoyl chlorides can be prepared by addition reaction between hexafluoropropylene or trifluorochloroethylene and a mono-, di-, or trihydroxy-substituted benzoic acid ester in the presence of a solvent and a base, subsequent alkaline hydrolysis to form the free acid, and finally conversion of the acid into the acid chloride e.g. by refluxing in the presence of thionyl chloride.

The addition reaction can be performed at a pressure between 1 and 14 bar and a temperature varying between room temperature and 150° C.

The base used in the addition reaction is e.g. sodium hydroxide, potassium hydroxide, sodium carbonate, potassium carbonate or an analogous inorganic base as well as an organic nitrogen-containing base such as triethylamine, N,N-dimethylaniline, or tetramethylguanidine.

The solvent used in the addition reaction is preferably aprotic and can be chosen from acetone, acetonitrile, tetrahydrofuran, dioxan, dimethylformamide, dimethylacetamide, N-methylpyrrolidone, hexamethylphosphorus triamide, or mixtures thereof.

Sometimes it is possible to perform the addition reaction of hexafluoropropylene or trifluorochloroethylene directly with a mono-, di-, or tri-hydroxy-substituted benzoic acid instead of a benzoic acid ester. Of course, this appropriately substituted benzoic acid can be converted directly into the acid chloride.

Preparation examples of the above-described addition reaction and the subsequent hydrolysis (if needed) can be found in the European Patent Application 0,015,592. Additionally, the synthesis of 4-(1,1,2,3,3,3-hexafluoropropyloxy)-benzoyl chloride is given in preparation 1 hereinafter for illustrative purposes.

The analogous fluoroalkylthio- or fluoroalkylsulphonyl-substituted benzoyl chlorides are prepared by addition reaction between hexafluoropropylene or trifluorochloroethylene and methyl-substituted thiophenols or mercapto-substituted benzoic acid esters. In the case of methyl-substituted thiophenols the benzoic acid derivatives have to be formed via known ways. For instance, the methyl group of such methyl-substituted thiophenols can be oxidized as described in step 2c of preparation 2 with the aid of potassium permanganate in a solvent mixture of pyridine and water or of tert-butanol and water.

In the addition reactions described above saturated Rf structures are normally obtained, but during the alkaline hydrolysis hydrogen fluoride may split off sometimes so that unsaturated Rf-groups e.g. —CF$_2$—CF=CF$_2$ may form in a random manner.

Preparation 1:

4-(1,1,2,3,3,3-hexafluoropropyloxy)-benzoyl chloride

1(a) 4-(1,1,2,3,3,3-hexafluoropropyloxy)-benzoic acid methyl ester 456 g (3 moles) of 4-hydroxybenzoic acid methyl ester, 30 g of 85% potassium hydroxide, and 1 l of acetone were placed in an autoclave. An amount of 562.5 g (3.75 moles) of hexafluoropropylene was introduced under pressure.

After agitation for 8 hours at 100°–105° C. the reaction mixture was poured out in 3 l of water. The oil layer was separated off and the water layer extracted with dichloromethane. The dried dichloromethane solution was evaporated to dryness and the residue together with the oil layer was distilled. The final product was distilled at 78°–82° C./0.5 mm.

Yield: 829.5 g.

1(b) 4-(1,1,2,3,3,3-hexafluoropropyloxy)-benzoic acid 570 ml of 5 N (2.85 moles) of potassium hydroxide were added at reflux temperature in 20 min to a solution of 430 g (1.42 mole) of starting product 1a) in 1425 ml of methanol. After 2 h 30 min of refluxing the solution was poured out in 4.5 l of icewater and 1.6 l of 5 N hydrochloric acid. The precipitate was filtered, washed until free from acid, and dried.

Yield: 267 g. Melting point: 143°–145° C.

1(c) 4-(1,1,2,3,3,3-hexafluoropropyloxy)-benzoyl chloride

A mixture of 57.6 g (0.2 mole) of intermediate product 1(b) and 150 ml of thionyl chloride was refluxed for 3 hours. Subsequently, the solvent was evaporated. The residue was distilled.

Yield: 50 g . Boiling point: 113°–121° C./11 mm.

The starting compounds listed in table 1 and corresponding to the following formula III:

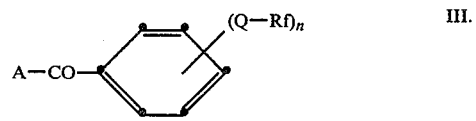

were prepared analogously to preparation 1.

TABLE 1

| A | (Q—Rf)$_n$ | |
|---|---|---|
| H$_3$CO | 2,4-di(—OCF$_2$CHFCF$_3$) | boiling at 124–130° C./3 mm |
| HO | 2,4-di(—OCF$_2$CHFCF$_3$) | oil |
| Cl | 2,4-di(—OCF$_2$CHFCF$_3$) | boiling at 114° C./0.2 mm |
| C$_2$H$_5$O | 3,4,5-tri(OCF$_2$CHFCF$_3$) | boiling at 130–132° C./2 mm |
| HO | 3,4,5-tri(OCF$_2$CHFCF$_3$) | oil |
| Cl | 3,4,5-tri(OCF$_2$CHFCF$_3$) | boiling at 118–123° C./0.7 mm |
| H$_3$CO | 2,4-di(—OCF$_2$CHFCl) | boiling at 161–162° C./5 mm |
| HO | 2,4-di(—OCF$_2$CHFCl) | melting at 69–70° C. |
| Cl | 2,4-di(—OCF$_2$CHFCl) | boiling at 162–167° C./12 mm |
| H$_3$CO | 2-OCF$_2$CHFCl | boiling at 123–125° C./5 mm |
| HO | 2-OCF$_2$CHFCl | melting at 79° C. |
| Cl | 2-OCF$_2$CHFCl | boiling at 138° C./17 mm |
| H$_3$CO | 4-OCF$_2$CHFCl | boiling at 149° C./15 mm |
| HO | 4-OCF$_2$CHFCl | melting at 168° C. |

TABLE 1-continued

| A | (Q—Rf)$_n$ | |
|---|---|---|
| Cl | 4-OCF$_2$CHFCl | boiling at 139° C./15 mm |

Preparation 2:
4-(1,1,2-trifluoro-2-chloroethylsulphonyl)benzoyl chloride

2(a) 4-(1,1,2-trifluoro-2-chloroethylthio)toluene

A hot solution (60° C.) of 248 g (2 moles) of 4-methylthiophenol, 44.8 g of 85% potassium hydroxide, and 280 ml of acetone were placed in an autoclave. An amount of 256 g (2.2 moles) of trifluorochloroethylene was introduced in 1 h under pressure with agitation at 50°–55° C. After 1 h the reaction mixture was poured out in a solution of 1200 ml of water and 80 g (2 moles) of sodium hydroxide. The final product was extracted with ether, the ether solution was dried, and the solvent was evaporated. The residual oil was distilled at 120° C./1 mm.

Yield: 300 g.

2(b) 4-(1,1,2-trifluoro-2-chloroethylsulphonyl)toluene

A mixture of 200 g of a 30% by volume solution of hydrogen peroxide in 100 ml of acetic acid was added dropwise in 30 min to a hot solution (40° C.) of 120 g (0.5 mole) of starting product 2(a) in 650 ml of acetic acid. The resulting solution was refluxed for 2 h and then poured out in 2 l of water. The precipitate was filtered off, washed until free from acid, and dried.

Yield: 131 g. Melting point: 80° C.

2(c) 4-(1,1,2-trifluoro-2-chloroethylsulphonyl)benzoic acid 43.5 g (0.275 mole) of potassium permanganate was added portionwise at 90° C. in 1 h to a solution of 27.25 g (0.1 mole) of intermediate product 2(b), 33 ml of pyridine, and 33 ml of water. After subsequent stirring for 2 h at 90° C. the manganese dioxide formed was filtered off while hot and the filtrate was acidified with 100 ml of concentrated hydrochloric acid. The precipitate was filtered off, dried, and recrystallized from a mixture of water and acetone.

Yield: 15 g. Melting point: 214° C.

2(d) 4-(1,1,2-trifluoro-2-chloroethylsulphonyl)benzoyl chloride

A mixture of 24.2 g (0.08 mole) of intermediate product 2(c) and 40 ml of thionyl chloride was refluxed for 4 h. After evaporation of the thionyl chloride the residue was distilled at 130° C./0.2 mm.

Yield: 22.9 g. Melting point: 60° C.

In the general formulae of the compounds listed hereinafter in table 2, the structures given for the fluorine-containing groups (Rf) are the apparent structures established by gas chromatographic analysis techniques. According to high pressure liquid chromatography it was found however, that a given Rf-group can have one of the structures given hereinbefore and even that mixtures of compounds with such different structures for the Rf-group are obtained. This means that in a compound the Rf-groups may be same or different. As described above this is due to the fact that hydrogen fluoride may split off from the saturated Rf-chain during the alkaline hydrolysis so that unsaturated Rf-groups may form in an unpredictable way.

Nevertheless it was found that these differences in the Rf structures of any compound or mixture of compounds according to the invention do not influence the characteristics of such compound or mixture as a colour coupler. Consequently, it is not necessary to separate the different fractions. Yet, they could be separated and used individually, if desired.

Representative examples of novel cyan-forming colour couplers corresponding to the above general formula I are given in the following table 2. It is to be understood, however, that the invention is not limited to these specific colour couplers.

TABLE 2

Compounds according to the above-mentioned general formula I:

| no. | (Q—Rf)$_n$ | X | Z | Melting at (in °C.) |
|---|---|---|---|---|
| 1 | 2,4-di(—O—CF$_2$CHFCl) | 2,4-di-(tert.C$_5$H$_{11}$—C$_6$H$_3$(—OCH(C$_4$H$_9$)— | H | 155 |
| 2 | 2,4-di(—O—CF$_2$CHFCl) | 2,4-di-(tert.C$_5$H$_{11}$—C$_6$H$_3$)—OCH(C$_4$H$_9$)— | Cl | 93–130 |
| 3 | 2-O—CF$_2$CHFCl | 2,4-di-(tert.C$_5$H$_{11}$—C$_6$H$_3$)—OCH(C$_4$H$_9$)— | H | 183 |
| 4 | 4-O—CF$_2$CHFCl | 2,4-di-(tert.C$_5$H$_{11}$—C$_6$H$_3$)—OCH(C$_4$H$_9$)— | H | 105 |
| 5 | 3,4,5-tri(—O—CF$_2$CHF—CF$_3$) | 2,4-di-(tert.C$_5$H$_{11}$—C$_6$H$_3$)—OCH(C$_4$H$_9$)— | H | 151–3 |
| 6 | 4-O—CF$_2$CHFCF$_3$ | 2,4-di-(tert.C$_5$H$_{11}$—C$_6$H$_3$)—OCH(C$_4$H$_9$)— | H | 119 |
| 7 | 2,4-di(—OCF$_2$CHFCF$_3$) | 2,4-di-(tert.C$_5$H$_{11}$—C$_6$H$_3$)—OCH (C$_4$H$_9$)— | H | 71–3 |
| 8 | 4-SO$_2$—CF$_2$CHFCl | 2,4-di-(tert.C$_5$H$_{11}$—C$_6$H$_3$)—OCH(C$_4$H$_9$)— | H | 176 |
| 9 | 2,4-di(OCF$_2$CHFCl) | 2,4-di-(tert.C$_5$H$_{11}$—C$_6$H$_3$)—OCH$_2$— | H | 192 |
| 10 | 4-O—CF$_2$CHFCF$_3$ | 2,4-di-(tert.C$_5$H$_{11}$—C$_6$H$_3$)—OCH$_2$— | H | 228 |
| 11 | 4-SO$_2$—CF$_2$CHFCl | 2,4-di-(tert.C$_5$H$_{11}$—C$_6$H$_3$)—OCH$_2$— | H | 240 |
| 12 | 2,4-di(—OCF$_2$CHFCF$_3$) | 2,4-di-(tert.C$_5$H$_{11}$—C$_6$H$_3$)—OCH(CH$_3$)— | H | 171 |
| 13 | 4-SO$_2$—CF$_2$CHFCl | 2,4-di-(tert.C$_5$H$_{11}$—C$_6$H$_3$)—O—(CH$_2$)$_3$— | H | 251 |
| 14 | 4-SO$_2$—CF$_2$CHFCl | 4-(tert.C$_4$H$_9$)—2-cyclopentyl-C$_6$H$_3$OCH(CH$_3$)— | H | 203 |
| 15 | 2,4-di(OCF$_2$CHFCF$_3$) | 3,5-dimethyl-4,4-dimethyl-chroman-6-yl —O—CH(C$_2$H$_5$)— | H | 76 |
| 16 | 3,4,5-tri(OCF$_2$CHFCF$_3$) | 3-(n-C$_{15}$H$_{31}$—C$_6$H$_4$)—OCH(C$_2$H$_5$)— | H | oil |
| 17 | 4-SO$_2$—CF$_2$CHFCl | 3-(n-C$_{15}$H$_{31}$—C$_6$H$_4$)—OCH—(C$_2$H$_5$)— | H | 142 |
| 18 | 4-O—CF$_2$CHFCl | 2,4-di-(tert.C$_5$H$_{11}$—C$_6$H$_3$)—OCH(C$_2$H$_5$)— | H | 155 |
| 19 | 2,4-di(—O—CF$_2$CHFCl) | 2,4-di-(tert.C$_5$H$_{11}$—C$_6$H$_3$)—OCH(C$_2$H$_5$)— | H | 115 |
| 20 | 3,4,5-tri(—OCF$_2$CHFCF$_3$) | 2,4-di-(tert.C$_5$H$_{11}$—C$_6$H$_3$)—OCH( C$_2$H$_5$)— | H | 70–90 |
| 21 | 4-OCF$_2$CHFCF$_3$ | 2,4-di-(tert.C$_5$H$_{11}$—C$_6$H$_3$)—OCH(C$_2$H$_5$)— | H | 168 |
| 22 | 2,4-di(—OCF$_2$CHFCF$_3$) | 2,4-di-(tert.C$_5$H$_{11}$—C$_6$H$_3$)—OCH(C$_2$H$_5$)— | H | 158 |
| 23 | 4-SO$_2$—CF$_2$CHFCl | 2,4-di-(tert.C$_5$H$_{11}$—C$_6$H$_3$)—OCH(C$_2$H$_5$)— | H | 209 |

TABLE 2-continued

Compounds according to the above-mentioned general formula I:

| no. | (Q—Rf)$_n$ | X | Z | Melting at (in °C.) |
|---|---|---|---|---|
| 24 | 4-SO$_2$—CF$_2$CHFCl | 2,4-di-(tert.C$_5$H$_{11}$—C$_6$H$_3$)—OCH(C$_2$H$_5$)— | Cl | 187 |
| 25 | 4-SO$_2$—CF$_2$CHFCl | 4-tert.C$_4$H$_9$—2-cyclopentyl-OCH(CH$_3$)— | Cl | 230 |
| 26 | 2,4-di(—O—CF$_2$CHFCl) | 2,4-di-(tert.C$_5$H$_{11}$—C$_6$H$_3$)—OCH(C$_2$H$_5$)— | 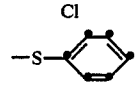 | 130–138 |
| 27 | 4-O—CF$_2$CHFCl | H$_2$C=C(CH$_3$)— | H | 240 |

The above cyan-forming coupler compounds can be prepared by condensing appropriately substituted benzoyl chlorides as described above with 2-amino-5-nitrophenol. After reduction of the nitro group by catalytic hydrogenation, the resulting 5-amino compound is condensed with an acid chloride carrying (a) ballasting group(s) that render(s) the colour coupler non-diffusing as referred to above.

For illustrative purposes the preparation of some of the cyan-forming couplers of the invention is given hereinafter. The preparation of other couplers according to the invention can be derived from these preparation examples and will not cause difficulties to those skilled in the art of preparative organic chemistry.

Preparation 3: Compound 1

3(a)
2-o,p-di(1,1,2-trifluoro-2-chloroethoxy)benzamido-5-nitrophenol 81.1 g (0.2 mole) of o,p-di(1,1,2-trifluoro-2-chloroethoxy)benzoyl chloride prepared as described in U.K. Patent Specification 1,236,767 and dissolved in 80 ml of acetone were added in 40 min to a suspension of 30.8 g (0.2 mole) of 2-amino-5-nitrophenol, 16.8 g (0.2 mole) of sodium hydrogen carbonate, and 320 ml of acetone. The temperature rose to 27° C. The reaction mixture was poured out with stirring in 1200 ml of icewater and 100 ml of concentrated hydrochloric acid. The resulting precipitate was filtered off, rinsed until free from salt, and dried.

Yield: 101 g. Melting point: 225° C.

3(b)
2-o,p-di(1,1,2-trifluoro-2-chloroethoxy)benzamido-5-aminophenol 328.5 g (0.628 mole) of compound 3(a) and 12.5 ml of Raney nickel suspension were diluted in an autoclave with methanol to a total volume of 1.5 l. The reduction was carried out with hydrogen gas at 75°–80° C. and an initial pressure of 100 to 105 bar. After 90 min of agitation the theoretical volume of hydrogen gas needed for the reduction of the nitro group was consumed. The catalyst was filtered off while hot and the filtrate was concentrated by evaporation. A brown solidifying oil was obtained.

3(c)
2-o,p-di(1,1,2-trifluoro-2-chloroethoxy)benzamido-5-[2-(2,4-di-tert.pentyl-phenoxy)hexanamido]-phenol (compound 1)

In 1 h a solution of 189 g (0.515 mole) of 2-(2,4-di-tert.pentyl-phenoxy)hexanoyl chloride in 400 ml of dioxan was added dropwise to a solution of 260 g (0.515 mole) of compound 3b), 122 g (1.03 mole) of distilled quinoline, and 2575 ml of dioxan. The mixture was stirred for 2 h at room temperature and left standing overnight. The reaction mixture was poured out in a mixture of 2880 ml of 2 N hydrochloric acid and 12.3 l of icewater. A sticky product precipitated. The liquid was decanted and the residue extracted with ether. The solution was dried. After evaporation of the solvent the precipitate was stirred in 1600 ml of boiling hexane. After cooling the precipitate was filtered off and recrystallized from 500 ml of nitromethane.

Yield: 252 g. Melting point: 135° C.

Preparation 4:
2-o,p-di(1,1,2-trifluoro-2-chloroethoxy)benzamido-4-chloro-5-[2-(2,4-di-tert.pentyl-phenoxy)hexanamido]-phenol (compound 2)

A solution of 41.15 g (0.05 mole) of compound 1 (see preparation 3) and 4.1 ml (0.0505 mole) of sulphuryl chloride in 125 ml of dry dichloromethane was stirred for 1 h at room temperature. The solution was concentrated by evaporation and the residue recrystallized from 70 ml of cyclohexane.

Yield: 25 g. Melting point: 120°–130° C.

The chlorination of compounds 24 and 25 was analogous to that of compound 2.

Preparation 5:
2-[p-(1,1,2-trifluoro-2-chloroethylsulphonyl)]-benzamido-5-nitrophenol A solution of 290 g (0.904 mole) of 4-(1,1,2-trifluoro-2-chloroethyl-sulphonyl)-benzoyl chloride in 360 ml of acetonitrile was added in 50 min to a suspension of 139.2 g (0.904 mole) of 2-amino-5-nitrophenol, 101 g (0.904 mole) of (1,4-diazobicyclo[2,2,2]octane) and 1450 ml of acetonitrile. The temperature rose to 45° C. As soon as the dissolution was complete, the solution was refluxed for 2 h and then poured out in 2700 ml of water and 900 ml of concentrated hydrochloric acid. The filtered product was rinsed until free from acid, dried, and purified by stirring in 500 ml of isopropyl ether.

Yield: 371 g. Melting point: 205° C.

Starting compounds and intermediate compounds listed in table 3 and corresponding to the formula IV:

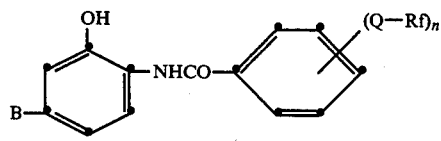

were prepared analogously to compounds 3a and 3b (see preparation 3) and the compound of preparation 5 respectively.

TABLE 3

| (Q—Rf)$_n$ | B=NO$_2$ | | B=NH$_2$ |
|---|---|---|---|
| | Reaction medium | Melting at (in °C.) | Melting at (in °C.) |
| 2-OCF$_2$CHFCl | NaHCO$_3$/acetone | 232 | 188 |
| 4-OCF$_2$CHFCl | NaHCO$_3$/acetone | 235 | 190 |
| 4-OCF$_2$CHFCF$_3$ | (1,4-diazabi-cyclo[2,2,2]-octane)/CH$_3$CN | 187 | 187 |
| 2,4-di(OCF$_2$CHFCF$_3$) | NaHCO$_3$/acetone | 212 | 115 |
| 3,4,5-tri(OCF$_2$CHFCF$_3$) | NaHCO$_3$/acetone | 172–182 | 135 |
| 4-SO$_2$CF$_2$CHFCl | (1,4-diazabicyclo-[2,2,2]octane/CH$_3$CN | 205 | 178 |

Preparation 6: compound 26

39.75 g (0.05 mole) of compound 19 of table 2 and a catalytic amount of iron powder were placed in a reaction flask that was completely shielded from light. The mixture was stirred in 65 ml of acetonitrile. Only part of compound 19 dissolved. The mixture was cooled with an ice-bath. A solution of 10.4 g (0.072 mole) of benzene sulphenyl chloride in 30 ml of acetonitrile was added dropwise in 30 min. At the end of the addition, dissolution was complete. The solution was stirred for 7 hours and left standing overnight. The precipitate was filtered with suction, washed with acetonitrile and n-hexane, and dried.

Yield: 10.5 g.

Preparation 7: compound 27

9.24 g (0.11 mole) of methacryloyl chloride were added at room temperature to a suspension of 36.05 g (0.1 mole) of 2-[4-(1,1,2-trifluoro-2-chloroethoxy)ben-zamido]-5-aminophenol, 9.24 g (0.11 mole) of sodium hydrogen carbonate, 1 ml of nitrobenzene and 80 ml of acetone. After having been stirred for 2 h, the light-yellow reaction mixture was poured out in water and neutralized with acetic acid. The precipitate was filtered off and dried. After recrystallization from acetonitrile 31.8 g of 2-[4-(1,1,2-trifluoro-2-chloroethoxy)benzamido]-5-methacrylamido-phenol (compound 27) melting at 240° C. were obtained.

Compound 27 is suited for use as a polymeric coupler in the form of a latex obtained by emulsion polymerization techniques with the aid of the usual addition polymerization initiators. Interesting polymerization techniques have been described e.g. in the Belgian Pat. No. 669,971, according to which latices are formed of polymeric colour couplers by emulsion polymerization in aqueous gelatin, and in the United Kingdom Patent Specification 1,130,581 according to which latices are formed of polymeric couplers by emulsion polymerization in water, as well as in the United Kingdom Patent Specification 1,453,057, according to which latices are made of polymeric colour couplers and competing couplers wherein the polymer particles are internally stabilized in the aqueous colloidal dispersion by a polymerically combined emulsifier.

Examples of polymerization initiators and suitable solvents as well as information relating to the formation of the initial emulsions and/or suspensions have been set forth in the above-mentioned patents.

The preparation of a latex polymer from compound 27 of table 2 can be carried out as follows. 9.3 ml of a 1% by weight solution of the sodium salt of 4,4′-azobis(4-cyanovaleric acid) as an initiator were added to 200 ml of demineralized water at 90° C. The solution was heated to 95° C. Next, 1/6th of a suspension of 30 g of 2-[4-(1,1,2-trifluoro-2-chloroethoxy)benzamido]-5-methacrylamido-phenol, 37.5 ml of 10% N-oleyl-N-methyltauride sodium salt, and 100 ml of water were added at once. In 15 min 1/6th of a mixture of 33.75 g of ethyl acrylate and 15 g of methacrylic acid was added on the one side and 4.7 ml of the above-mentioned initiator solution were added dropwise on the other side. The temperature was kept at 94°–96° C.

The addition of 1/6th of the above suspension and of the mixture of ethyl acrylate and methacrylic acid as well as 4.7 ml of initiator solution was repeated five times. The mixture was then heated for 30 min at reflux temperature and the latex was concentrated by evaporation for 10%.

Yield: 336 g of latex polymer of 2-[4-(1,1,2-trifluoro-2-chloroethoxy)benzamido]-5-methacrylamino-phenol, ethyl acrylate, and methacrylic acid.

Concentration of solids per 100 g of latex: 13.8 g
Concentration of polymer per 100 g of latex: 12.6 g.

The term "non-diffusing" used herein has the meaning commonly applied to the term in photography and means that in any practical application migration or wandering of such non-diffusing coupler compound through organic colloid layers in an alkaline medium, such as gelatin, in the photographic elements of the invention is substantially unexisting.

For the preparation of a photographic multilayer colour element the non-diffusing colour couplers for each of the colour separation images are usually incorporated into the coating compositions of the differently sensitized silver halide emulsion layers. Yet, the non-diffusing colour couplers can also be added to the coating compositions of non-light-sensitive colloid layers that are in water-permeable relationship with the light-sensitive silver halide emulsion layers.

During the preparation of the light-sensitive colour element the non-diffusing cyan-forming colour couplers according to the above general formula can be incorporated in the coating composition of the silver halide emulsion layers or other colloid layers in water-permeable relationship therewith according to any technique known by those skilled in the art for incorporating photographic ingredients, more particularly colour couplers, into colloid compositions.

The cyan-forming colour couplers according to the invention can be dispersed, occasionally in the presence of a wetting or dispersing agent, in a hydrophilic composition constituting or forming part of the binding agent of the colloid layer. Very suitable wetting agents that can be used to disperse the cyan-forming colour couplers of the invention are the fluorine-containing surface active agents of U.K. Patent Application No. 79/07040 filed on 28th Feb., 1979. For more details about particularly suitable techniques that can be employed for incorporating the colour couplers of the invention into a hydrophilic colloid layer of a photographic element there can be referred to U.K. Patent Specifications 791,219-1,098,594-1,099,414-1,099,415-1,099,416-1,099,-417-1,199,570-1,218,190-1,297,947, to the U.S. Pat. Nos. 2,269,158-2,284,887-2,304,939-2,304,940-2,322,027, to the French Patent No. 1,555,663, and to the Belgian Pat. No. 722,026.

Another technique for incorporating colour couplers is via polymeric latices as described in the published German Patent Applications DE-OS 2,541,230 and 2,541,274 and as referred to hereinbefore.

The cyan-forming colour couplers according to the invention can be used in conjunction with various kinds of photographic emulsions. Various silver salts can be used as the light-sensitive salt. For instance silver bromide, silver iodide, silver chloride or mixed silver halides such as silver chlorobromide, silver bromoiodide, and silver chlorobromoiodide can be employed. The couplers can be used in emulsions of the mixed packet type as described in the U.S. Pat. No. 2,698,794, or emulsions of the mixed grain type as described in the U.S. Pat. No. 2,592,243. The colour couplers can be used with emulsions wherein latent images are formed predominantly at the surface of the silver halide crystal or with emulsions wherein latent images are formed predominantly inside the silver halide crystal.

The hydrophilic colloid used as the vehicle for the silver halide can be e.g. gelatin, colloidal albumin, zein, casein, a cellulose derivative, a synthetic hydrophilic colloid such as polyvinyl alcohol or poly-N-vinyl pyrrolidone. If desired, compatible mixtures of two or more of these colloids can be employed for dispersing the silver halide.

The light-sensitive silver halide emulsions used in the preparation of a photographic material according to the present invention can be sensitized chemically as well as optically. They can be sensitized chemically by carrying out the ripening in the presence of small amounts of sulphur-containing compounds such as allyl thiocyanate, allyl thiourea, or sodium thiosulphate. The emulsions can also be sensitized by means of reducing agents e.g. tin compounds as described in the French Patent No. 1,146,955 and in the Belgian Patent No. 568,687, imino-aminomethane sulphinic acid compounds as described in U.K. Patent Specification 789,823 and small amounts of noble metal compounds such as gold, platinum, palladium, iridium, ruthenium, and rhodium compounds. They can be sensitized optically by means of cyanine and merocyanine dyes.

The said emulsions can also comprise compounds that sensitize the emulsions by development acceleration e.g. compounds of the polyoxyalkylene type such as alkylene oxide condensation products as described i.a. in U.S. Pat. Nos. 2,531,832 and 2,533,990, in U.K. Patent Specifications 920,637-940,051-945,340-991,608 and 1,091,705 and onium derivatives of amino-N-oxides as described in U.K. Patent Specification 1,121,696.

Further, the emulsions may comprise stabilizers e.g. heterocyclic nitrogen-containing thioxo compounds such as benzothiazoline-2-thione and 1-phenyl-2-tetrazoline-5-thione and compounds of the hydroxytriazolopyrimidine type. They can also be stabilized with mercury compounds such as the mercury compounds described in Belgian Pat. Nos. 524,121-677,337, and in the U.K. Patent Specification 1,173,609.

The light-sensitive emulsions containing the colour couplers of the invention may also comprise any other kind of ingredient such as those described for such emulsions in Research Disclosure no. 17643 of December 1978, in particular development-inhibitor-releasing compounds and competing couplers. Such compounds and couplers can be incorporated in layers in water-permeable relationship with the emulsion layers containing the couplers of the present invention.

The non-diffusing cyan-forming colour couplers of the present invention are usually incorporated into a red-sensitized silver halide emulsion for forming one of the differently sensitized silver halide emulsion layers of a photographic multilayer colour element. Such photographic multilayer colour element usually comprises a support, (a) red-sensitized silver halide emulsion layer(s) with cyan-forming colour coupler, (a) green-sensitized silver halide emulsion layer(s) with magenta-forming colour coupler, and (a) blue-sensitive silver halide emulsion layer(s) with yellow-forming colour coupler.

The emulsions can be coated on a wide variety of photographic emulsion supports. Typical supports include cellulose ester film, polyvinylacetal film, polystyrene film, polyethylene terephthalate film and related films or resinous materials, as well as paper and glass.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilized as developers. Suitable developing agents are aromatic compounds in particular p-phenylene diamines e.g. N,N-diethyl-p-phenylene diamine; N,N-dialkyl-N',N'-di-(2-hydroxyethyl)-p-phenylene diamines; N,N-dialkyl-N'-sulphomethyl-p-phenylene diamines; and N,N-dialkyl-N'-carboxymethyl-p-phenylene diamines.

The following example illustrates the present invention.

EXAMPLE 114.6 g of a red-sensitized silver bromoiodide emulsion (2.3 mole % of iodide) comprising per kg an amount of 73.4 g of gelatin and an amount of silver halide equivalent to 47 g of silver nitrate were diluted with 127 g of a 7.5% by volume solution of gelatin in 100 ml of distilled water.

A dispersion of cyan-forming colour coupler was made by dissolving 0.006 mole of the colour coupler as specified in table 4 hereinafter in 16 ml of ethyl acetate and 2 g of dibutylphthalate, dispersing the resulting solution in 100 ml of a 5% by volume aqueous solution of gelatin containing 0.4 g of the sodium salt of dodecylbenzene sulphonic acid by means of an ultrasonic power generator, and eliminating the ethyl acetate by evaporation under reduced pressure.

The resulting dispersion was added to the red-sensitized silver halide emulsion.

After neutralization of the emulsion and addition thereto of the usual additives such as stabilizing agents e.g. 5-methyl-7-hydroxy-s-triazolo[1,5-a]pyrimidine, wetting agents, and hardening agents the necessary amount of distilled water to obtain 575 g of emulsion was added.

The emulsion was coated on a film support in a ratio of 150 g per sq.m. The emulsion layer was dried and covered with a gelatin antistress layer. The dried emulsion material was cut and the resulting strips were exposed in a Herrnfeld sensitometer for 1/20th second through a continuous wedge with a constant of 0.30. The exposed strips were colour-developed, bleached, fixed, and washed in the conventional way using 2 different types of developers viz.:
the first developer containing as developing agent 2-amino-5-diethylamino-toluene hydrochloride (CD-2); development time: 10 minutes; temperature of development: 24° C., the second containing as developing agent 4-amino-N-ethyl-N-(β-methanesulphonamidoethyl)-m-toluidine sesquisulphate monohydrate (CD-3); development time: 15 minutes; temperature of development: 21° C.

In table 4 hereinafter the values of speed, gradation and maximum density obtained after processing with the above-mentioned developers of the strips of red-sensitized emulsion containing the cyan-forming couplers are given.

Colour coupler A is compared in table 4 hereinafter with compounds 5, 9, 15, 19, and 22 respectively.

TABLE 4

| cyan-forming coupler in red-sensitized emulsion | Sensitometric results | | | | | |
|---|---|---|---|---|---|---|
| | CD 2 | | | CD 3 | | |
| | Speed | Gradation | $D_{max}$ | Speed | Gradation | $D_{max}$ |
| comparison* coupler A | 100 | 1.6 | 2.9 | 100 | 2.0 | 2.7 |
| compound 5 | 63 | 1.7 | 3.2 | 100 | 1.9 | 3.0 |
| compound 9 | 100 | 1.4 | 2.9 | 63 | 1.7 | 2.8 |
| compound 15 | 200 | 1.8 | 3.6 | 200 | 2.1 | 3.2 |
| compound 19 | 158 | 1.3 | 2.8 | 50 | 1.6 | 2.4 |
| compound 22 | 158 | 1.6 | 3.1 | 158 | 1.7 | 2.7 |

*Comparison coupler A is 5-[α-(2,4-di-tert-pentylphenoxy)hexanamido]-2-heptafluorobutyramidophenol, which is a coupler according to the U.S. Pat. Specification 2,895,826.

The speed was measured at 0.2 above fog. The values given for the speed are relative values, a value of 100 being given to the emulsion containing the comparison coupler A.

It appears from the results in table 4 that in general the speed, gradation, and maximum density of the photographic elements containing the coupler compounds according to the invention are at least as good as those of the elements containing the comparison coupler A.

A light stability test of the cyan dyes obtained with the cyan-forming colour couplers of table 4 gave the results listed in table 5.

The losses in density (expressed in %) of the cyan wedges obtained with the above-mentioned developers were measured at density 0.5 and 1.5 after exposure for 15 h to a 1500 W Xenon lamp in a XENONTEST 150 apparatus marketed by Original Hanau Quartzlampen GmbH, Hanau am Main, Federal Republic of Germany.

TABLE 5

| cyan wedge from | CD 2 developer | | CD 3 developer | |
|---|---|---|---|---|
| | 0.5 | 1.5 | 0.5 | 1.5 |
| comparison coupler A | −43 | −23 | −34 | −17 |
| compound 5 | −6 | −9 | −4 | −10 |
| compound 9 | −5 | −5 | −1 | 0 |
| compound 15 | −5 | −7 | −4 | −4 |
| compound 19 | −6 | −6 | −4 | −2 |
| compound 22 | −5 | −7 | −3 | −2 |

It appears that the light-stability of the cyan images obtained from the cyan-forming colour couplers of the invention is superior to that obtained from the comparison coupler A.

We claim:

1. Photographic element comprising (a) light-sensitive silver halide emulsion layer(s) and at least one phenol-type colour coupler capable of forming a cyan indoaniline dye by reaction with an oxidized aromatic primary amino developing agent and carrying a fluorine-containing substituent, wherein said colour coupler comprises in the 2-position of the phenol a benzamido group carrying on its benzene nucleus at least one —Q—Rf group as fluorine-containing substituent, Q being oxygen, sulphur, or sulphonyl, and Rf representing a short-chain fluorine-containing group derived from hexafluoropropylene or trifluorochloroethylene, such short-chain group corresponding to one of the formulae: —CF$_2$—CHFY, —CF=CFY, or —CF$_2$—CF=CF$_2$, Y being chlorine or trifluoromethyl.

2. Photographic element according to claim 1, wherein said colour coupler corresponds to the following general formula:

X—CONH—[phenol ring with OH, Z]—NHCO—[benzene ring]—(Q—Rf)$_n$ wherein:
n represents an integer of at least 1,
Z represents a hydrogen atom or a coupling off group, and
X is a ballasting group of sufficient size rendering said colour coupler non-diffusing in an alkali-permeable layer of a photographic element.

3. Photographic element according to claim 2, wherein in said colour coupler Z is selected from the group consisting of a halogen atom, an acyloxy group, an alkoxy group, an aryloxy group, a heterocycloxy group, an alkylthio group, an arylthio group, an alkylsulphonyl group, an arylsulphonyl group, an alkylsulphinyl group, an arylsulphinyl group, an alkyl- or aryl-substituted carbonylmethoxy group, an alkoxy- or aryloxy-substituted carbonylmethoxy group, a heterocyclic thio group, and a phenylazo group.

4. Photographic element according to claim 2, wherein in said colour coupler X is a ballasting group corresponding to the general formula:

[benzene ring with R$^2$, R$^3$ substituents]—R$^1$—O—A wherein:
A is a C$_1$-C$_5$ alkylene group,
R$^1$ is hydrogen or a C$_1$-C$_5$ alkyl group,
R$^2$ is a halogen atom, an alkyl group, an alkoxy group, or a cycloaliphatic group,
R$^3$ is hydrogen or an alkyl group, or
R$^2$ and R$^3$ together represent the atoms needed to complete a fused on cycloaliphatic ring or a fused on cycloaliphatic ring that is substituted by up to 4 alkyl groups.

5. Photographic element according to claim 1, wherein said element is a photographic multilayer colour element comprising at least three silver halide emulsion layers, which are differently optically sensitized, the red-sensitized silver halide emulsion layer or a non-light-sensitive colloid layer in water-permeable relationship therewith incorporating said phenol-type colour coupler.

* * * * *